(12) United States Patent
Hill (10) Patent No.: US 11,730,916 B1
(45) Date of Patent: Aug. 22, 2023

(54) DEVICE AND SYSTEM FOR HANDS FREE MONITORING AND COMFORTING

(71) Applicant: Robert Hill, Towson, MD (US)

(72) Inventor: Robert Hill, Towson, MD (US)

( * ) Notice: Subject to any disclaimer, the term of this patent is extended or adjusted under 35 U.S.C. 154(b) by 0 days.

(21) Appl. No.: 17/952,673

(22) Filed: Sep. 26, 2022

Related U.S. Application Data (60) Provisional application No. 63/358,209, filed on Jul. 4, 2022.

(51) Int. Cl.
*A61M 21/00* (2006.01)

(52) U.S. Cl.
CPC ..... *A61M 21/00* (2013.01); *A61M 2021/0022* (2013.01); *A61M 2021/0027* (2013.01); *A61M 2205/3584* (2013.01); *A61M 2230/005* (2013.01); *A61M 2230/04* (2013.01); *A61M 2230/50* (2013.01)

(58) Field of Classification Search
CPC ................................................ A61M 21/00–02
See application file for complete search history.

(56) References Cited

U.S. PATENT DOCUMENTS

| | | | | |
|---|---|---|---|---|
| 11,478,606 B1 * | 10/2022 | English | ................. | A61M 21/02 |
| 2020/0147339 A1 * | 5/2020 | Mayo | ................... | A61M 21/02 |
| 2021/0023332 A1 * | 1/2021 | Auger | ................... | A61B 5/165 |

FOREIGN PATENT DOCUMENTS

| | | | |
|---|---|---|---|
| CN | 201011894 Y | * | 1/2008 |
| KR | 101959683 B1 | * | 3/2019 |

OTHER PUBLICATIONS

English Translation of KR 101959683 B1. (Year: 2019).*

* cited by examiner

*Primary Examiner* — Thaddeus B Cox
(74) *Attorney, Agent, or Firm* — Whiteford, Taylor & Preston, LLP; Gregory M. Stone (57) ABSTRACT

Light weight, compact, battery powered, body-worn devices and systems are configured to allow automated, hands-free monitoring and care intervention, such as of an infant, by providing audio and/or physical stimulus when a negative comfort or health condition is detected by the body-worn device and system, and by monitoring the infant's temperature, pulse, and oxygen levels. The body-worn device preferably includes a flexible printed circuit board ("FPCB") that allows the device to be conformed to the wearer's body, and has a plurality of linear resonant actuators affixed to the FPCB that are configured to impart soothing vibrations from the device to the wearer. A control program is provided and executable on a remote computing device, which control program is configured to enable users (such as a caregiver) to selectively control the actuators. The device may include a water-resistant casing covering its internal components, including the actuators, FPCB, battery, and those portions of on-board sensors not intended for direct monitoring contact with the wearer.

19 Claims, 6 Drawing Sheets

DEVICE AND SYSTEM FOR HANDS FREE MONITORING AND COMFORTING

CROSS-REFERENCE TO RELATED APPLICATIONS

This application claims the benefit of U.S. Provisional Patent Application No. 63/358,209 titled "Nan-e WIRELESS SOOTHING DEVICE & GENERAL WELLNESS MONITOR," filed by the inventor herein on Jul. 4, 2022, the specification of which is incorporated herein by reference in its entirety.

FIELD OF THE INVENTION

The present invention relates generally to devices and systems for infant monitoring and care, and more particularly to body-worn devices and related systems for remote monitoring of an infant's condition and automatic care intervention.

BACKGROUND

Crying babies have long created stress for both the unhappy or uncomfortable baby and their caregivers. While there may be many causes at any time, those causes can be difficult to discern, particularly given the lack of understanding between the parents or caregivers and the infant. One prior study by Johns Hopkins University has noted that most babies cry between one to five hours in a 24-hour period, noting the most common causes as including hunger, tiredness, having a dirty or wet diaper, being too hot or too cold, or simply being bored. The stress caused by the infant's crying can be particularly stressful when the caregiver is called to tasks other than caring for the infant (e.g., when the infant is in a crib, baby swing or play chair, etc.). Still further, such stress can be yet even more stressful when the infant wakes crying in the middle of the night.

In order to aid parents and caregivers in this effort, various products have been commercially provided to help calm a crying infant. For example, while infant monitors can inform caregivers in another room that the infant is, at a minimum, unhappy as evidenced by crying; however, such monitors still require the caregiver to get out of bed or stop their other activity to care for the infant. Other products, such as vibrating chairs, vibrating mats and mattress pads, vibrating teething rings, and the like have been provided in the hopes of having the vibrations generated from such devices soothe or calm the child. In fact, many parents have undertaken the practice of putting a crying baby into a vehicle and driving until the vibrations from the vehicle soothe the infant back to sleep. In a prior study, researchers developed a driving simulator capable of precisely replicating the vibrations caused by driving on standard sealed roads. The report from such research noted that during the test, "by looking at the volunteers' heart rate variability (HRV), the researchers were able to gain an objective measure of how drowsy they were feeling as the 60-minute test progressed. Within 15 minutes of starting the vibrating test, volunteers were showing signs of drowsiness. Within 30 minutes, the drowsiness was significant, requiring substantial effort to maintain alertness and cognitive performance."

While vibrating devices thus may assist in inducing drowsiness (whether in an infant or adult), it does not resolve all of the possible conditions that might cause an infant discomfort or pain that would induce them to cry. For example, the management of pain after eating caused by gas may, for some infants, be quite painful and difficult to manage without physical intervention, and event widely applied vibrations (such as from vibrating mattress pads, teething rings, or even vehicle rides) will not soothe the infant in such pain, with resolution typically requiring hands-on intervention from the caregiver to burp, massage, and otherwise physically soothe the crying infant.

Thus, there remains a need in the art for devices and systems capable of monitoring an infant's comfort and health, and in response to detecting some negative aspect of their comfort or health, automatically employ a hands-free soothing intervention configured to help resolve the negative condition.

SUMMARY OF THE INVENTION

Disclosed are body-worn devices and related systems configured to allow automated, hands-free monitoring and care intervention, such as of an infant, by providing audio and/or physical stimulus when a negative comfort or health condition is detected by the body-worn device and system (e.g., when the device and system detect that the infant is crying, restless, has an abnormal temperature, etc.), and by monitoring the infant's temperature, pulse, and oxygen levels. The body-worn device wirelessly communicates with a control program, such as a software application executable on a portable, remote computing device such as a smartphone, tablet, laptop, or any similarly configured computing device, which control program may record physiological and general health data of the infant, generate alerts for a caregiver and display in real-time the infant's current vitals, regulate and track schedules of recommended prearranged essential activities, log developmental milestones, and generally allow the caregiver to remotely interact with the body-worn device to control its functions. The control program may also interact with communications devices on the computing device to, by way of non-limiting example, upload data that has been recorded from the device to a cloud data storage facility, share data with individuals selected by the caregiver (such as for example the infant's pediatrician), and automatically alert emergency services in the event that a life-threatening condition is detected (such as an excessively low heart rate or low oxygen level over a predetermined amount of time). In certain exemplary embodiments, the control program may allow the caregiver to access an online-hosted community discussion forum, consumer review networks, media sharing social media blogs, and such other online communities as will occur to those of ordinary skill in the art.

In accordance with an exemplary embodiment of the invention, systems, methods, and devices are provided that are configured to wirelessly soothe an infant and monitor the infant's vitals. In exemplary configurations, such systems, methods and devices automatically soothe an infant without requiring the caregiver to physically contact the infant themselves. Likewise in exemplary configurations, such systems, methods and devices may monitor specifically the infant's blood oxygen level, heart rate, and body temperature and generate an alert for the caregiver when an abnormal measure is detected. Still further in exemplary configurations, such systems, methods and devices may wirelessly soothe infants and enable wireless monitoring of the infant's vitals.

A device according to certain aspects of an embodiment of the invention may include a vibrating mechanism and sensing module housed within a removable, body-worn and thus wearable technology. Vibrating motors inside of the device, such as linear resonant actuators, and the sensing module are housed within a preferably flexible protective enclosure, with the motors, sensors, and other components mounted to a flexible substrate, such as a flexible printed circuit board ("FPCB") to enable the device to conform to the infant's body, such as directly on the infant's stomach. The device may be placed on the infant's skin using an adhesive, such as one or more preferably medical grade, non-allergenic adhesive two-sided tape strips or an adhesive disc, enabling the direct transfer of vibrations from the device to the infant's body and direct monitoring of the infant's skin to determine the infant's body temperature, heart rate, blood oxygen level and sleep quality. The device also preferably includes a processing unit that receives and processes data indicative of the infant's body temperature, heart rate, and blood oxygen level for monitoring purposes and to determine whether any of the sensed conditions indicate the need for intervening, automatic care or the generation of one or more alerts. The device also preferably includes a wireless transmitter in communication with the processing unit. The wireless transmitter is configured to transmit the foregoing infant's vitals to a receiving station, such as a remote, portable computing device of the caretaker, or optionally a separate, fixed receiving station. Preferably in each case, the receiving station calculates and categorizes the collected infant vitals data to identify trends that suggest the infant is uncomfortable, or health concerns evidence by the infant's vitals, and may deploy interventions that are tailored towards the detected condition. For example, the receiving station may generate an alarm for the caregiver, may automatically take an intervening action at the device (such as to engage a particular vibratory cycle among the array of vibratory motors, play sounds, recorded voices, or music, automatically alert third parties such as medical personnel and emergency medical service), or may prompt the caregiver (such as directly through an audio or visual alert generated by the caregiver's remote computing device) to initiate any such intervening actions at the device.

In accordance with still further aspects of an exemplary embodiment of the invention, the system provides a processing unit that communicates with the wearable device via a wireless transceiver. The processing unit may present a user with various functions that may be engaged via selected buttons on a user interface, with each selectable button signifying a particular event associated with the device wearer. When an event occurs, the user may engage the selectable button (e.g., press a "button" shown on a display of the user interface) to have the event, and the time and date on which the event occurred, logged into memory. The logged data may then be further processed to compile multiple events and provide numerical and/or graphical information regarding the various events. Additionally, the processing unit may allow the user, such as a caregiver, to record finite information such as quantity of food/milk consumed, breast being used for feeding, volume, duration and/or diet consumed and expelled. This collected data allows for the software to analyze and calculate the temperament of the baby. The prearranged essential activities may be based on accumulated data on infants collected from industries that specifically analyze infantile behavior, milestones, diet, and all concerns that parents and caregivers may have. The software additionally can provide a space to enter questions and receive answers based off of information provided from the industries' accumulated data. Additionally, users may speak to the device to add notes, wake the baby, burp the baby and more in the present time or future.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
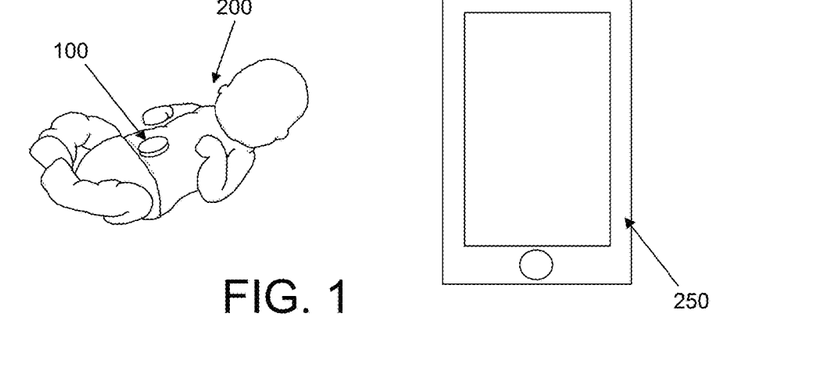
FIG. 1 is a schematic view of a device and system for hands free monitoring and comforting in accordance with certain aspects of an embodiment of the invention.

In accordance with certain aspects of an exemplary embodiment and with reference to the schematic view of FIG. 1, a wearable combination sensor and soothing device 100 is provided, along with a user interface operable on a remote computing device 250, such as a caregiver's smartphone, to receive data from the device and allow a user to interact with and control the device 100.

By way of summary, the device 100 is a small, body-worn, wireless soothing and monitoring unit configured to allow automated, hands-free monitoring and care intervention, such as of an infant 200, by monitoring the infant's temperature, pulse, oxygen levels, and preferably sleep condition (e.g., in order to detect interrupted sleep), and by providing physical and/or audio stimulus when a negative comfort or health condition is detected by the body-worn device and system (e.g., when the device and system detect that the infant is crying, restless, has an abnormal temperature, etc.).

Figure 2:
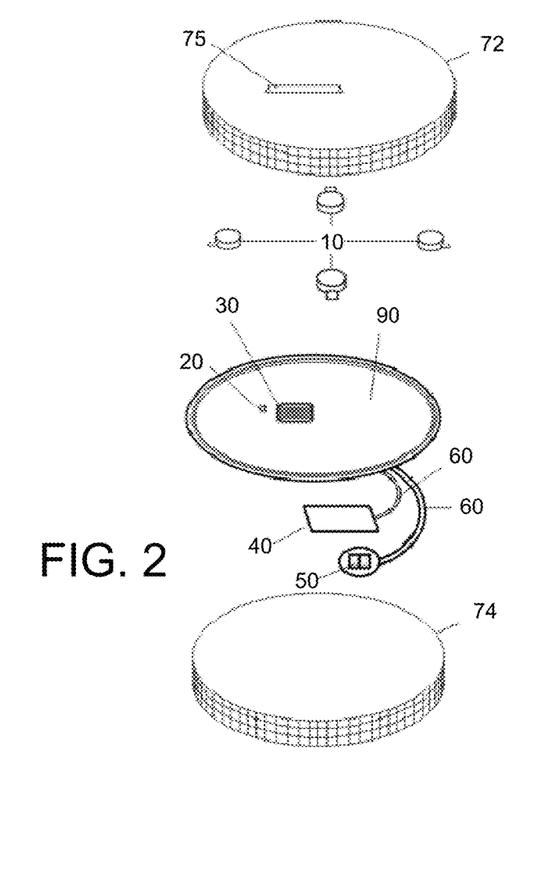
FIG. 2 is an exploded view of the device for hands free monitoring and comforting of FIG. 1.
Figure 3:
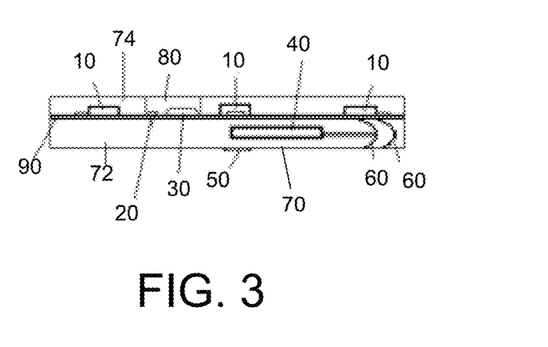
FIG. 3 is a side, cross-sectional view of the device for hands free monitoring and comforting of FIG. 1.
Figure 4A:
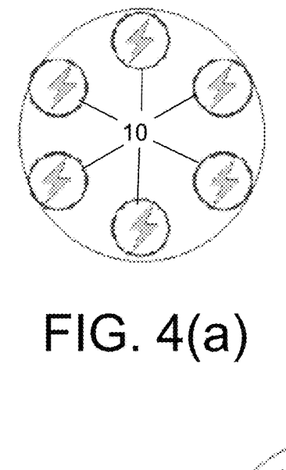
FIGS. 4(a)-4(d) are schematic views of activation cycles of vibratory motors in the device for hands free monitoring and comforting of FIG. 1.
Figure 4B:
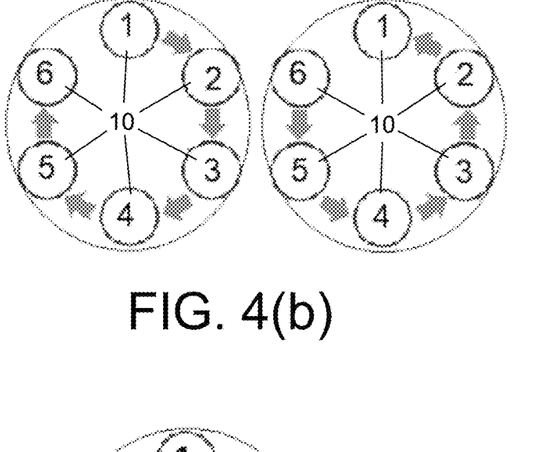
Figure 4C:
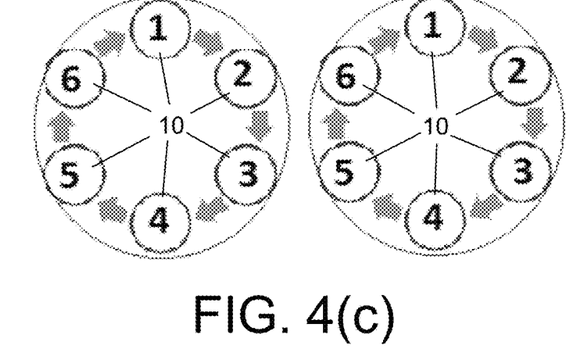
Figure 4D:
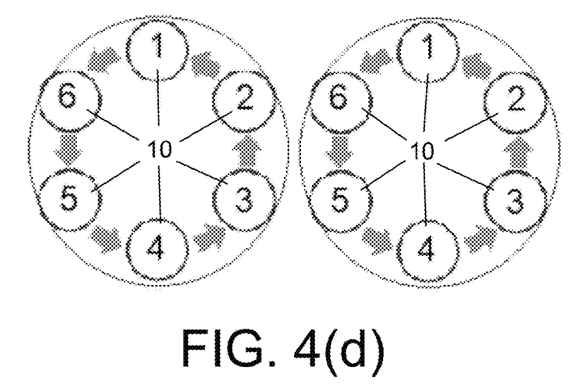
Figure 5:
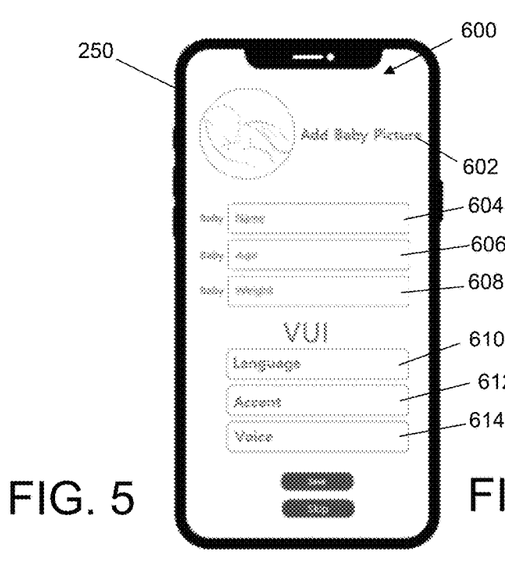
FIGS. 5-11 are exemplary user interface screens enabling interaction with a control application executable on the remote computing device in the system of FIG. 1.

In accordance with certain aspects of an embodiment of the invention and with particular reference to FIGS. 2 and 3, at least a portion of the soothing function of device 100 may be provided by a plurality of vibratory motors 10, such as a plurality of linear resonant actuators (also known as linear vibrators). Such vibratory motors 10 are common electric components the construction of which is well known to those of ordinary skill in the art, such that their specific configurations are not detailed further here. Vibratory motors 10 are mounted in a circumferential pattern to a flexible printed circuit board ("FPCB") 90, which FPCB is housed within a soft housing 70 formed of preferably a waterproof or water resistant material and comprising a body facing casing portion 72 and a non-body facing casing portion 74. Each of body-facing casing portion 72 and non-body facing casing portion 74 is preferably formed of a medical-grade gel material (many of which are readily commercially available and adaptable to use as housing 70), and having a thickness preferably in the range of 10 mm to 15 mm. In such configuration, housing 70 provides additional cushion for vibrations imparted by vibratory motors 10 to the wearer. Moreover, housing 70 protects the FPCB and the components mounted to FPCB inside of housing 70, enabling both easy application of device 100 to an infant and removal of device 100 from the infant, in addition to easy replacement of components inside of device 100 as needed. Body-facing casing portion 72 of housing 70 includes an opening 75 configured to align with one or more sensors 50 on FPCB (discussed in greater detail below) to enable detection of desired vital readings directly from the wearer's skin.

It is notable that given the flexible substrate of flexible printed circuit board ("FPCB") and the flexible outer housing 70, device 100 is readily able to conform to the infant's (or other wearer's) body, such as directly on the infant's stomach, thus maximizing the flexibility in where and ease with which the device 100 may be applied.

In an exemplary embodiment, device 100 may be applied to the infant's skin using an adhesive, such as one or more preferably medical grade, non-allergenic adhesive two-sided tape strips or a similarly configured, double-sided adhesive disc, which materials are readily commercially available. In exemplary configurations, the adhesive may be applied to the infant's skin for up to 24 hours without negative effect on the infant. Such adhesive member joins device 100 to the infant to enable the direct transfer of vibrations from the device 100 to the infant's body and direct monitoring of the infant's skin to determine the infant's body temperature, heart rate, blood oxygen level, and sleep state. Such adhesive member is preferably disposable and water-resistant. A first side of the adhesive member may be applied to body-facing casing portion 72 of housing 70, and the second, opposite side of the adhesive member may be applied to the infant's skin. The adhesive member also includes an opening that aligns with opening 75 in body-facing casing portion 72, and thus likewise also aligns with one or more sensors 50 on FPCB (discussed in greater detail below) to enable detection of desired vital readings directly from the wearer's skin.

As noted above, device 100 includes monitoring sensors 50 configured to detect the physical condition of the infant that may be indicative of a discomfort condition. The sensors 50 in device 100 include a pulse oximeter configured to measure the infant's blood oxygen level and heart rate. As is known to those of ordinary skill in the art, pulse oximeter sensors are readily commercially available and provide an uncomplicated and inexpensive optical measurement method for heart rate monitoring purposes, using photoplethysmography ("PPG") which is a non-invasive technology that uses a light source and a photodetector at the surface of skin to measure the volumetric variations of blood circulation, including arterial oxygen saturation ($SpO_2$). Sensors 50 also include a thermometer, such as (by way of non-limiting example) a touchless or remote thermometer, again the construction of which are well known to those of ordinary skill in the art and thus not discussed further here.

In certain exemplary configurations, sensors 50 may also include a touch-responsive sensor, such as a capacitive touch sensor positioned on flexible printed circuit board 90 that may be activated by contacting non-body facing casing portion 74 at the location of the capacitive touch sensor, and may communicate with the controller to cause at least one of vibratory motors 10 to vibrate for a period of time after the touch-responsive sensor has been contacted. As will be recognized by those of ordinary skill in the art, capacitive sensors detect the change of capacitance through the influence of external objects, such that coming into contact with the capacitive touch sensor (e.g., directly or through casing 70) will cause a change in voltage in the sensor, which change in voltage may be used as a control signal to initiate vibrations by at least one of vibratory motors 10. Thus and by way of non-limiting example, when the capacitive touch sensor is contacted, at least one of vibratory motors 10 may vibrate for a pre-determined period, such as by way of non-limiting example 2 seconds. Vibrations from the initiated vibratory motors 10 will be felt by the infant and detected by the controller. Vibrations caused by contact with the capacitive touch sensor may thus be used to train the infant to use device 100 as a communications device. Specifically, a caregiver may touch device 100 repeatedly during feeding, causing device 100 to vibrate for, for example, 2 seconds numerous times during that feeding so as to draw a mental association between the vibrational pulses and feeding. As the infant's motor skills develop, they may learn to touch device 100 to initiate those vibrations in anticipation of being fed, while the controller may detect the fact that the infant has touched device 100 and alert the caregiver (via remote computing device 250) that the infant is communicating that he or she wishes to eat. Further, the control program may cause device 100 to vibrate in differing patterns automatically during various events that, as discussed in greater detail below, comprise tracked and scheduled prearranged essential activities, such as by way of non-limiting example feeding, diaper changes, etc., such that the caregiver need not themselves repeatedly contact device 100 to associate a particular vibration pattern with the particular activity. Such repeated and automatic vibrations generated during those essential activities may draw associations in the infant's mind between the particular vibration pattern and the activity, aiding in further development of the infant's vocabulary. Those skilled in the art will recognize that combinations of different vibrational sequences may be used to further allow the infant to communicate different messages through similar training techniques as discussed above, and thus may readily be programmed by users through the control program to customize vibration patterns to varied activities as the caregiver may deem appropriate.

For optimal operation, in use device 100 configured with monitoring sensors 50 may be adhesively applied to an infant's abdomen. More particularly, for optimal operation device 100 should be positioned so as to enable sensors 50 to collect readings from the infants superior epigastric vessel ("SEV"), which is layered between the rectus abdominis muscle and the linea alba, generally located in the middle of the abdomen, which likewise positions device 100 parallel to the infant's digestive tract. Such positioning adjacent to the infant's digestive tract may be particularly important to enable vibrations generated by device 100 to aid in soothing digestive pain from gas after eating. More particularly and as further detailed below, vibrations from device 100 imparted to the infant's abdomen over their digestive tract will cause a rippling effect to promote movement of gas in the infant's digestive tract, thus resulting in hands-free burping of the infant.

Device 100 may further include a microphone 20 and a speaker 30 mounted to FPCB 90. Microphone 20 may monitor the wearer's immediate surroundings to detect that the wearer is upset, such as a crying infant when the wearer is an infant, thus enabling caregivers to monitor the sound environment of the infant or other device wearer from varied locations. Speaker 30 may be used to play pre-recorded messages in familiar voices (e.g., that of a caregiver), music, soothing sounds, sounds or recordings configured to aid in cognitive development, and such other sounds as may readily occur to those of ordinary skill in the art. For example, detection of crying sounds may first notify a caregiver via the control application of the fact that the infant is crying, and device 100 may simultaneously in response to such detection that the infant is crying cause vibratory motors to initiate vibrations, play prerecorded voice messages (e.g., from the infant's mother, father, nanny, etc. or manufacturer or user prerecorded soothing sounds) to soothe and generally calm the crying infant. Likewise, speaker 30 may be used to play one or more sounds or recordings, such as multi-language audio files, sounds or recordings configured to increase infant cognition, and such other messages as may occur to those skilled in the art. All such recordings will preferably be stored in a remote data storage environment, such as a cloud data storage facility, although in certain configurations they may likewise be stored in a memory on device 100 or on computing device 250 as may be desirable in certain implementations without departing from the spirit and scope of the invention.

Still further, device 100 may include a power source 40, such as a rechargeable battery such as a LiPo battery that may supply power to device 100 and the foregoing components. Such rechargeable batteries and their connections to and integration with components in electronic devices are well known to those of ordinary skill in the art and thus are not further detailed here. Moreover, such battery assemblies may be recharged in a number of methods known to those of ordinary skill in the art, thought in a particularly preferred embodiment battery 40 of device 100 may be wirelessly recharged by placing device 100 on a readily commercially available cordless charger.

In certain configurations, device 100 may also include a gyroscope that may be used to determine the infant's body position, such as prone or supine, as well as an accelerometer to detect particular motions of the infant.

In response to the sensors 50 on FPCB 90 detecting some discomfort condition or other condition warranting intervention, one or more hands-free soothing interventions may automatically be applied by device 100. One such intervention may include activation of vibratory motors 10 in a predetermined activation pattern that is particularly adapted to address the specifically determined condition. For example and as further detailed below, in the event that the sensed conditions indicate that the wearing infant is in physical discomfort, such as from gas after eating, vibratory motors 10 may be activated in a manner that simulates burping and massaging of the infant's abdomen in order to reduce their discomfort. Likewise and as mentioned above, in the event that microphone 20 detects some discomfort condition (such as crying), device 100 may play pre-recorded sounds, messages, music, or other recordings through speaker 30 to soothe the infant back to calm or sleep.

In addition to the foregoing components, FPCB further mounts a communications module (not shown), such as a wireless transceiver capable of bi-directional communication with remote control unit 250. Such communications module is preferably configured to enable two-way wireless communication via one or more of BLUETOOTH or a similar short-range wireless interconnection, wireless Wi-Fi or similar network, a wide area network such as the Internet, or such other wireless communications devices and methods, whether now or future-existing, as will readily occur to those of ordinary skill in the art. The communications module thus enables both transmission and reception of voice and data signals, and particularly is configured to transmit data to and receive control signals from control unit 250. In this configuration, any data that may be collected from sensors 50 on device 100 may, in exemplary configurations, be transmitted from device 100 via the communications module to control device 250 and/or to a remote data storage facility, such as a cloud based data storage facility. Thus and by way of non-limiting example, any logged information (such as events requiring hands-free interventions, alerts generated, as well as general developmental milestones) may be sent from device 100 and stored in such remote data storage, and ultimately shared from such remote data storage with the user's preferred network, such as pediatricians, family members, and such other individuals or facilities in the caregiver's network as will occur to those of ordinary skill in the art.

The processor interfaces via the communications module with a control program, such as a software application executable on a portable, remote computing device 250 such as a smartphone, tablet, laptop, desktop computer, monitoring station, or any similarly configured computing device. The control program may receive from the wireless transceiver and either record or transmit to a remote data storage facility physiological and general health data of the infant, generate alerts for a caregiver, display in real-time the infant's current vitals, and generally allow the caregiver to remotely interact with the body-worn device to control its functions and engage desired, hands-free interventions to address detected distress or discomfort conditions being experienced by the infant wearing the device. In order to further enable hands-free operation, the control program may include a voice user interface ("VUI") that allows the user/caregiver to engage operations of the control program via voice commands given to either the remote computing device 250 or via the microphone 20 on device 100.

As noted above, when sensors on FPCB 90 detect a discomfort condition or other condition warranting intervention, one or more of the soothing interventions may be applied in an effort to calm and comfort the wearer of device 100. In order to determine whether and which such soothing interventions are to be applied, the processor may be programmed to simulate specific vibrating modes and sounds according to the infant's schedule. Thus and by way of non-limiting example, if an infant is going to sleep or if sleep was interrupted, the device 100 will initiate basic vibrating or, for example, the first listed lullaby or a combination of the two functions according to the battery life. Likewise, if the infant recently ate, the device 100 will initiate a clockwise vibrating function (discussed in greater detail below), and then if no burp is detected after, for example, two minutes a prompt will appear on the mobile device alerting the caregiver of a temporary one minute pause and follow with a thump vibration if no burp was detected or heard. After the second vibrating function halts, the caregiver will be presented a suggestion to reposition the infant. Still further, if the infant had recently awakened during the beginning of the day, the device will play the first listed soothing audio or a prerecorded audio from the caregiver's choice. Additionally, if the infant begins to show signs of discomfort or begins to cry, vibrations may be initiated. Of course, such exemplary vibrations and sound functions are exemplary only, and may be modified as desired in particular implementations without departing from the spirit and scope of the invention.

As noted above, a plurality of vibratory motors 10 are mounted, for example soldered, to the FPCB to impart soothing vibrations to the wearer, such as an infant 200, through the gel cushion casing bottom 70 of device 100. Vibratory motors 10 may be activated with specific vibratory sequences that may be particularly configured to address specific discomforts, distress, or other conditions that the system has determined that the infant or other individual is experiencing in real-time. More particularly, device 100 may be configured to activate vibratory motors 10 with varied start and stop points and overall vibration frequencies and patterns based on the detected condition and a data collection of vibratory patterns previously determined to soothe or otherwise ameliorate those detected conditions. Vibratory motors 10 may thus be activated in various specific sequences to mimic physical interactions in a hands-free manner, such as specific vibratory sequences that are configured to mimic burping actions or other physical soothing techniques. As the vibratory motors 10 are arranged in a circular or circumferential pattern around FPCB 90, they may be activated in differing patterns that may mimic, for example, circular patterns, patting patterns, heartbeat patterns, and the like as further described below.

With particular reference to FIG. 4, exemplary operational modes of vibratory motors 10 are shown that are configured to mimic specific physical interactions with the infant, particularly including activation sequences that provide soothing functions and that promote gas movement through the infant's intestinal tract. As shown in FIG. 4(*a*), a first operational mode may synchronously vibrate all vibratory motors 10 at the same time for ½ second to simulate a gentle hand thumping motion. As shown in FIG. 4(*b*), a second operational mode may vibrate the vibratory motors 10 sequentially, initially in a clockwise direction, and then in a counter-clockwise direction to simulate a vibrational pulse in two directions to further promote movement of gas in the infant's digestive tract. As shown in FIG. 4(*c*), a third operational mode may vibrate the vibratory motors 10 sequentially in a clockwise configuration to simulate a clockwise circular rubbing motion. Likewise as shown in FIG. 4(*d*), a fourth operational mode may vibrate the vibratory motors 10 sequentially in a counter-clockwise configuration to simulate a counter-clockwise circular rubbing motion. Optionally, still other vibration operational modes may be initiated, such as simultaneously activating all vibratory motors 10 repeatedly to simulate a person's heartbeat, and such other vibration patterns as may occur to those skilled in the art. Further, while in some configurations the vibrational patterns may loop for a designated period of time, such as by way of non-limiting example five minutes, the looping period is preferably adjustable to fit the particular needs of a user's/caregiver's application.

The control program may also regulate and track schedules of recommended prearranged essential activities, log developmental milestones, interact with communications devices on the computing device 250 to, by way of non-limiting example, upload data that has been recorded from the device to a remote data storage facility, such as a cloud data storage facility, share data with individuals selected by the caregiver (such as for example the infant's pediatrician), and automatically alert emergency services in the event that a life-threatening condition is detected (such as an excessively low heart rate or low oxygen level over a predetermined amount of time). In certain exemplary embodiments, the control program may allow the caregiver to access an online-hosted community discussion forum, consumer review networks, media sharing social media blogs, and such other online communities as will occur to those of ordinary skill in the art. Further, the control program may allow the user/caregiver to control and manage multiple devices configured as above at the same time.

Preferably, the control program may further analyze data collected from device 100 to form hypotheses relating to the device wearer's current condition. By way of non-limiting example, based upon various data collected from sensors 50, the control program may form hypotheses that the device wearer has had a bowel movement or has urinated and thus requires changing, or that the device wearer is currently sleeping, or such other conditions as those skilled in the art will recognize may reasonably be determined based upon data collected from sensors 50.

FIGS. 5 through 11 provide exemplary user interface screens enabling interaction with the control application executable on the remote computing device 250 as discussed above. First and with particular reference to FIG. 5, upon initiating the control application, a user may be presented initial prompt screen 600 that may enable the uploading of a photo of the infant via operation 602, and the data entry of the infant's name (operation 604), age (operation 606), weight (operation 608), and such other individual physical data (e.g., optionally gender, length, date of birth, etc.) as may readily occur to those of ordinary skill in the art. Such individual physical data may be used by the control application for various functions (e.g., tracking developmental milestones against established standards, selecting age- or development-stage-appropriate sounds and/or educational content for the infant, etc.). By way of non-limiting example, the infant's name may automatically be spoken through device 100 to familiarize them with their own name, to get the infant's attention, etc. Initial prompt screen 600 may also present the user with voice user interface (VUI) settings to enable hands-free, voice operation of the control application, including setting their language (operation 610), accent (operation 612), and voice (operation 614). Once those settings are established, the user may engage with the control application to apply functions including setting a current vibration mode, activating the device in an audio monitoring mode, activating the device in an audio recording mode, causing the device to play audio, causing the device to log developmental milestones, allowing a user to record notes, allowing a user to contact emergency medical services ("EMS") if necessary, and such other operations of the control application discussed herein as may be amenable to activation or control through voice activation. Preferably, the control application is configured to receive such voice commands both through microphone 20 of device 100 and through a microphone on remote computing device 250.

Figure 6:
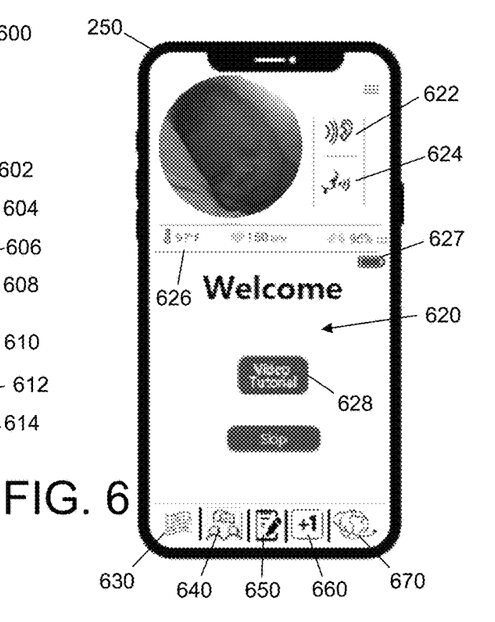

Following the presentation to the user of the initial prompt screen 600 discussed above (and upon startup of the control application for subsequent operation), the user may be presented welcome screen 620 as shown in FIG. 6. From welcome screen 620, a user may cause the control application to engage an audio monitoring operation 622 to hear audio received at microphone 20, and a talk operation 624 to remotely engage speaker 30 to allow the infant wearing device 100 to hear the speaker's voice through device 100. Welcome screen 620 also may present current, live physical condition data 626 reflecting current physical conditions of the monitored infant wearing device 100, including one or more of (by way of non-limiting example) the infant's temperature, hear rate, and/or oxygen level. Welcome screen 620 may further display current charge status 627 of battery 40, and an option to cause the control application to engage a video tutorial operation 628 that displays a recorded video explaining how to navigate and use the control application.

Welcome screen 620 also preferably includes a series of icons that may be engaged by the user to enable access to differing portions of the control application that each enable control of different monitoring and operational functions. More particularly, a soothing mode icon 630 will navigate the user to a soothing mode screen 631 (FIG. 7); an communication mode icon 640 will navigate the user to a communication mode screen 641 (FIG. 8); a planner and information log icon 650 will navigate the user to a planner and information log screen 651 (FIGS. 9(a)-9(c)); an add device icon 660 will navigate the user to an add device screen 661 (FIG. 10); and a network resources icon 670 will navigate the user to a network resources screen 671 (FIG. 11). Each of the foregoing will now be described in further detail.

Figure 7:
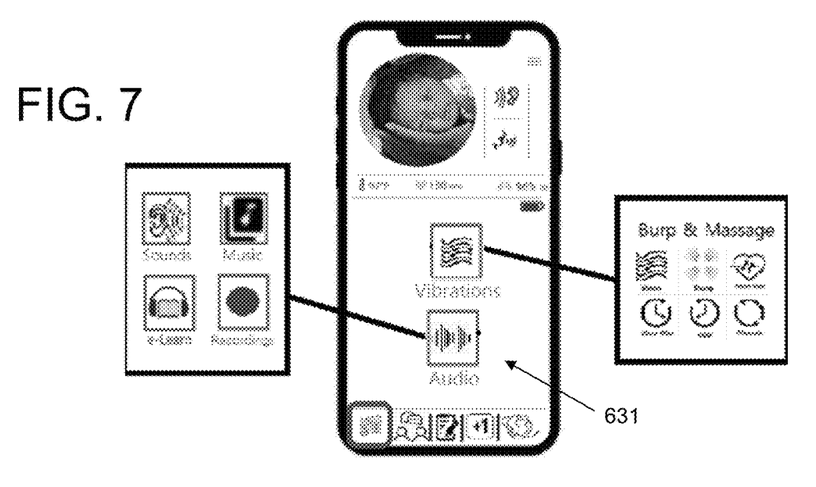
Figure 7A:
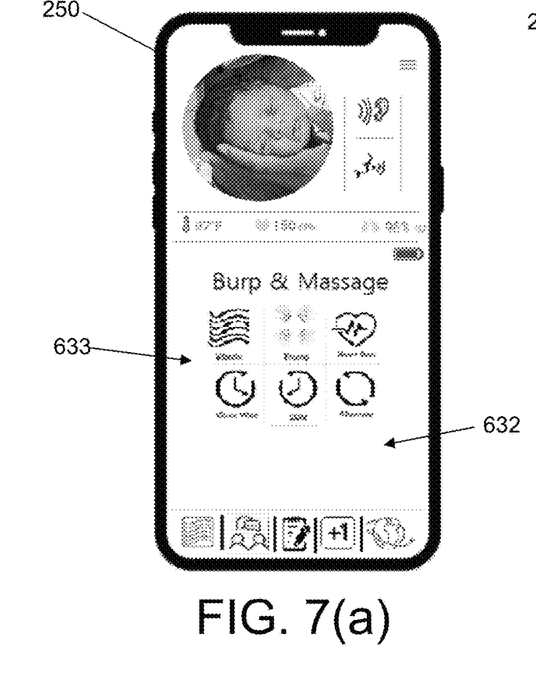
Figure 7B:
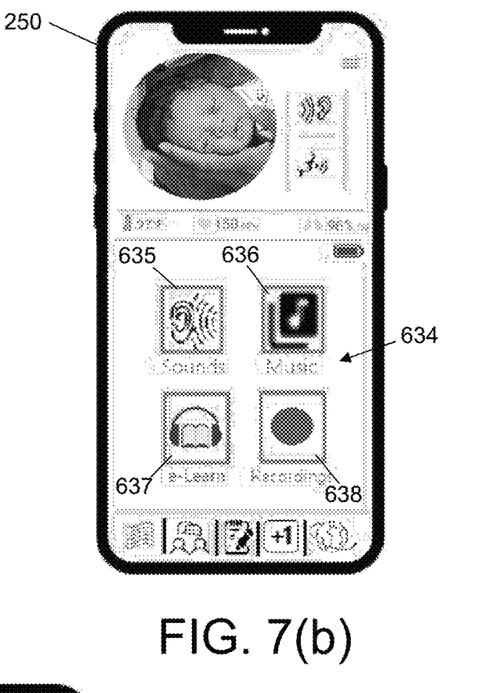

With reference to FIGS. 7, 7(a) and 7(b), soothing mode screen 631 may enable a user to cause the control application to engage various vibrational operational modes of vibratory motors 10 on device 100 by accessing vibrational mode scree 632 (FIG. 7(a)), and particularly the various vibrational operational modes discussed above with reference to FIGS. 4(a)-4(d). A series of icons 633 may be engaged by the user to select which of the various vibrational operational modes they wish to use at any given time. Preferably, each vibrational operational mode selected by one of icons 633 will loop according to a preset timer that may be adjusted by the user via the control application.

Likewise, soothing mode screen 631 may enable a user to cause the control application to play selected audio content via speaker 30 on device 100 by accessing audio mode screen 634 (FIG. 7(b)). More particularly, a first sounds icon 635 enables the user to choose from a stored library of various audio recordings comprising sounds configured to soothe and/or calm an infant. By way of non-limiting example, the user may elect to have the control application play white noise for a designated or selected period of time. A second music icon 636 enables the user to choose from a library of music (optionally including music stored on the user's portable computing device 250) to have such music played through speaker 30 on device 100. Preferably, the control application may have a recommended playlist of music from which users may select age-appropriate music to calm and soothe the infant. Further, a third e-learn icon 637 enables the user to choose from a stored library of audio content configured to aid cognitive development of the infant. By way of non-limiting example, such content may include an array of animal calls or sounds from nature, and such other cognitive development focused sounds as will occur to those skilled in the art. Likewise, such audio content may include sound recordings that are played from one designated side of device 100 to cause the infant to direct their attention to one side. After a designated period of such training, the generic directional sound may be replaced by, for instance, the word "LEFT" when the sound is directed from the left of device 100, and the word "RIGHT" when the sound is directed from the right of device 100, to aid the wearer in learning such directional terms. Still further, the audio content may include a particular sound that may be played during a particular event, such as just before feeding the infant, thus creating an association in the infant's mind between the particular sound and feeding time. Of course, other sounds may likewise be employed to aid in cognitive development as will occur to those skilled in the art. Finally, a fourth recordings icon 638 enables the user to choose from a library of recordings made by the user to aid in familiarizing the infant with the caregiver's or other individuals' voices, and such other recordings as a user may wish to playback to the infant.

Figure 8:
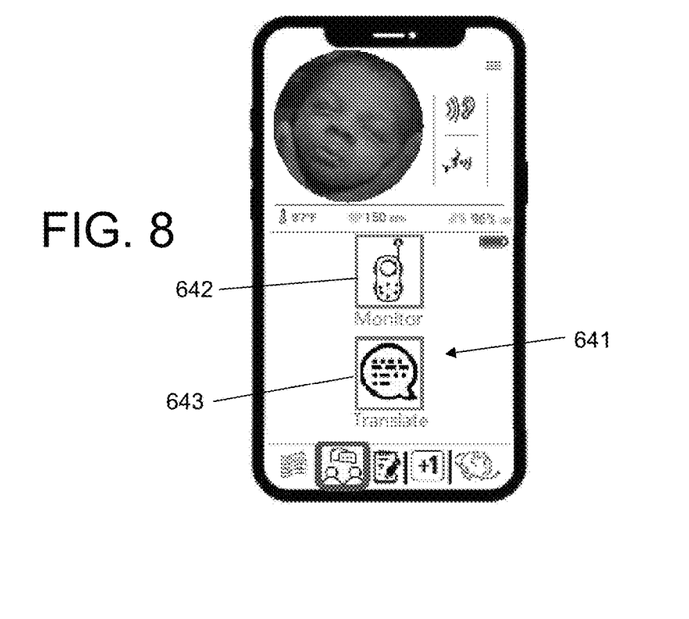

Next and with reference to FIG. 8, communication mode screen 641 may enable a user to cause the control program to initiate audio monitoring of the wearer of device 100 through microphone 20 through selection of a monitoring function 642, and to initiate a translation mode through selection of translation function 643. Translation function 643 may provide a list of words that are associated with differing vibrational sequences, such that when a user selects a word from the list, device 100 will initiate the vibrational sequence that is associated with that word. As noted above, the associations established in the infant's mind between vibrational sequences and particular activities aid in building vocabulary skills, and a caregiver may further reinforce the development of those skills by selecting words at appropriate times (e.g., during or just prior to feeding) and causing device 100 to engage the vibrational sequence associated with that word. To even further aid in advancing vocabulary skills, device 100 may additionally pronounce the words through speaker 30 when the word is selected and the vibrational sequence is initiated, and may in certain implementations pronounce the selected word in more than one language to further aid in advancing the infant's vocabulary.

Figure 9A:
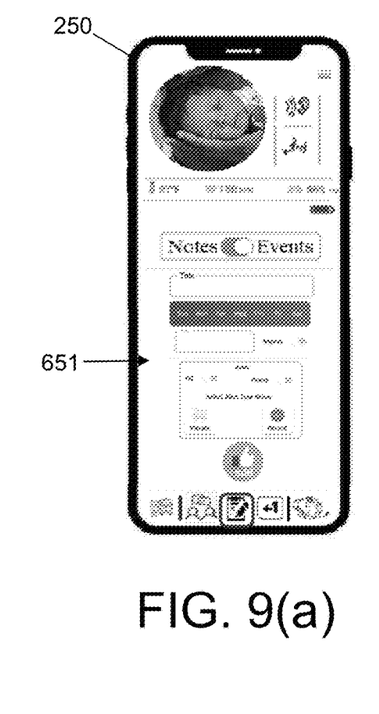
Figure 9B:
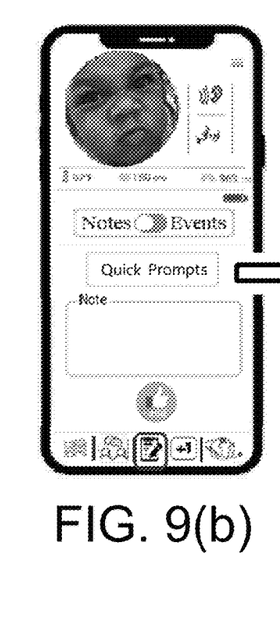
Figure 9C:
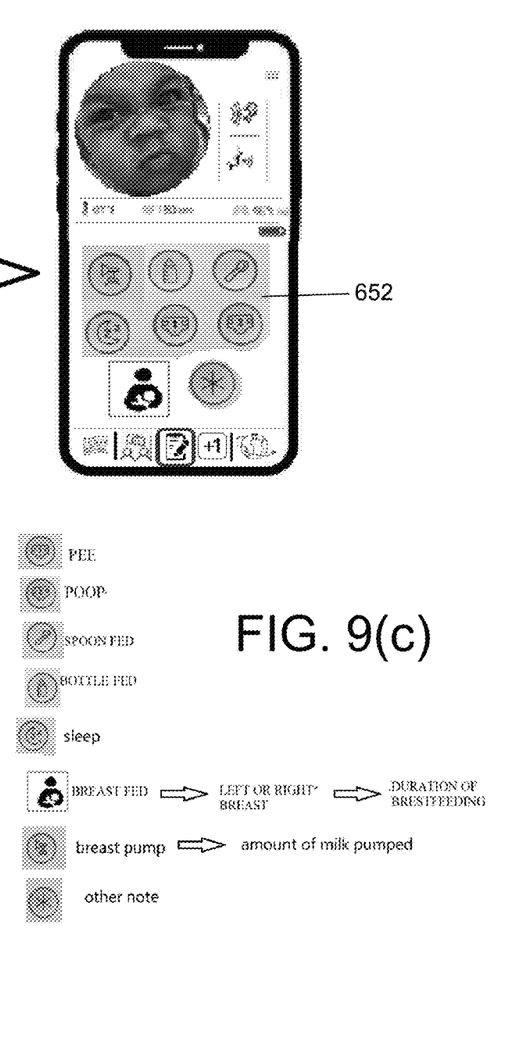

Next and with reference to FIGS. 9(a)-9(c), planner and information log screen 651 may enable a user to cause the control application to record data relating to various events and notes. As noted above, planner and information log screen 651 may communicate with device 100 via the wireless transceiver on device 100. As shown in FIG. 9(*a*), the user may plan particular events (e.g., feeding, naps, etc.), select a day and time at which such event is to take place, and select a format of an alert or reminder to carry out such event. As shown in FIG. 9(*b*), the user may manually (or verbally via the VUI) input notes relating to a specific event occurrence. Finally, as shown in FIG. 9(*c*), the user may select a particular event for which they wish to record notes from a plurality of icons 652 for quick access to commonly occurring events (as shown in the legend of FIG. 9(*c*)). In that regard, the control program may present a user with various functions that may be engaged via selected buttons on a user interface, with each selectable button signifying a particular event associated with the device wearer. When an event occurs, the user may engage the selectable button (e.g., press a "button" shown on a display of the user interface) to have the event, and the time and date on which the event occurred, logged into memory. The logged data may then be further processed to compile multiple events and provide numerical and/or graphical information regarding the various events. Additionally, the processing unit may allow the user, such as a caregiver, to record finite information such as quantity of food/milk consumed, breast being used for feeding, volume, duration and/or diet consumed and expelled. This collected data allows for the software to analyze and calculate the temperament of the baby. The prearranged essential activities may be based on accumulated data on infants collected from industries that specifically analyze infantile behavior, milestones, diet, and all concerns that parents and caregivers may have. The software additionally can provide a space to enter questions and receive answers based off of information provided from the industries' accumulated data. Additionally, users may speak to the device to add notes, wake the baby, burp the baby and more in the present time or future.

Figure 10:
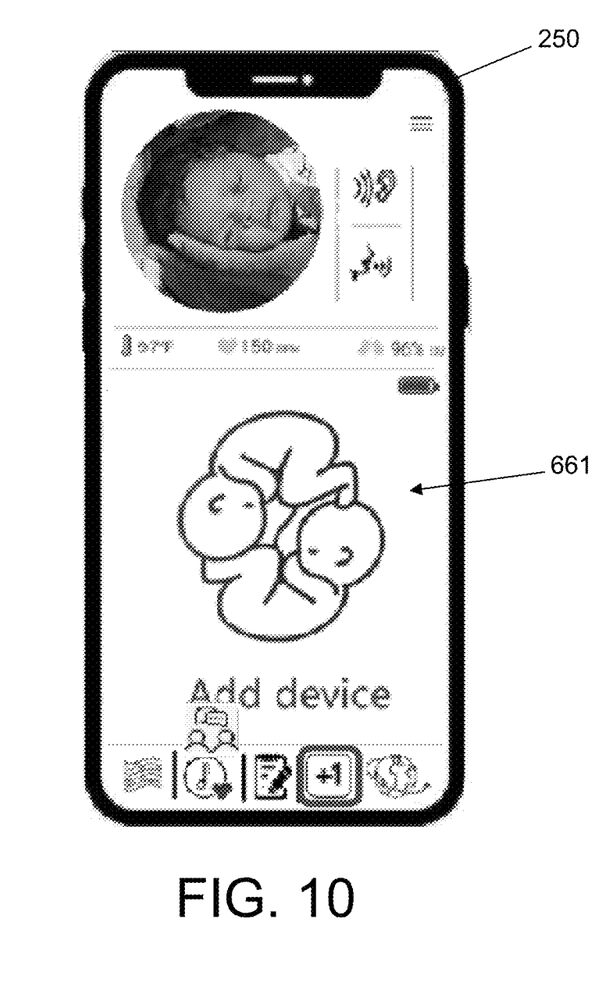
Figure 11:
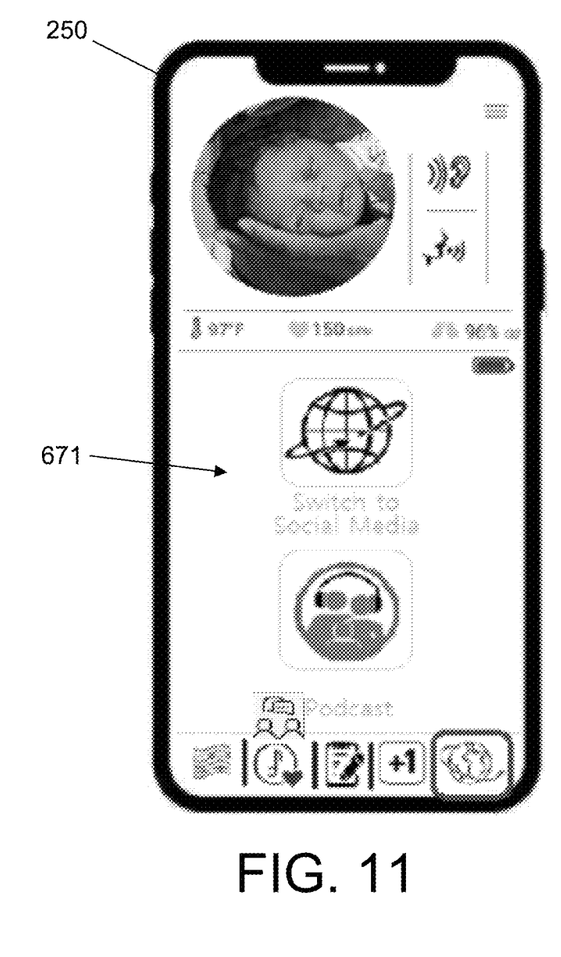

Next and with reference to FIG. 10, add device screen 661 may enable a user to cause the control application to connect to and control more than a single device 100 configured as above, with each device 100 having a separate profile managed by the control application to allow a user to optionally customize separate devices for different monitored individuals.

Finally and with reference to FIG. 11, network resources screen 671 may enable a user to cause the control application to access various media resources on an external network, such as a wide area network (such as the Internet). In an exemplary configuration, external media resources may include one or more social media applications enabling the user to engage with such social media applications through the control application. Likewise in an exemplary configuration, external media resources may include podcasts or related content enabling the user to view or play recorded podcasts through the control application.

While the foregoing operations reference engagement by the user's physical interaction with various icons, the control applications' VUI will likewise in preferably each instance allow the user to engage such functions through voice commands.

A device 100 and system employing such device 100 configured as above may have wide application, and is not limited to applications corresponding to any specific age range. Rather, device 100 and control unit 250 (and the control program thereon) may, by way of non-limiting example, be applicable to use in hospitals, long term care facilities, and any other facility in which it may be desirous to remotely monitor the health and comfort conditions of an individual and to initiate hands-free interventions when negative conditions are detected. The device 100 may thus be use in patients of all manner in addition to infants, such as individuals having various physical or mental disabilities, dementia patients, and the like. The use of device 100 and systems employing such device 100 configured as described herein may readily be adapted to the particular needs of the caregiver to address such a variety of conditions and situations.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. A device for hands-free monitoring and comforting of a person, comprising:
   a flexible housing;
   a flexible printed circuit board inside of said flexible housing;
   a processor attached to said flexible printed circuit board;
   at least one sensor attached to said flexible printed circuit board and configured to measure at least one physical condition of the person and to communicate said at least one measured physical condition to said processor; and
   a plurality of vibratory motors mounted to said flexible printed circuit board and arranged in a planar circular ring pattern on said flexible printed circuit board extending around a perimeter of said flexible printed circuit board;
   wherein said processor comprises executable instructions thereon configured to, in response to said at least one measured physical condition, selectively (i) sequentially actuate said plurality of vibrating motors in series along said circular ring pattern, and (ii) simultaneously activate multiple of said plurality of vibratory motors.

2. The device of claim 1, wherein each one of said plurality of vibratory motors is configured for independent activation.

3. The device of claim 2, wherein said device is configured to impart vibrations generated from said plurality of vibratory motors to the person through said flexible housing.

4. The device of claim 1, wherein said at least one sensor comprises at least a pulse oximeter sensor.

5. The device of claim 4, at least one sensor further comprising a thermometer.

6. The device of claim 1, said device further comprising:
   a microphone attached to said flexible printed circuit board; and
   a speaker attached to said flexible printed circuit board.

7. The device of claim 1, wherein an opening extends through a first side of said flexible housing, wherein said opening is aligned with said at least one sensor.

8. The device of claim 7, further comprising a multi-sided adhesive on said first side of said flexible housing adapted for removable application of said device to the person's skin.

9. The device of claim 1, further comprising a communications module in data communication with said at least one sensor and configured to communicate data generated at said at least one sensor to a remote device controller application.

10. A system for hands-free monitoring and comforting of a person, comprising:
   a wearable device, said wearable device comprising:
      a flexible housing;
      a flexible printed circuit board inside of said flexible housing;
      a processor attached to said flexible printed circuit board;
      at least one sensor attached to said flexible printed circuit board and configured to measure at least one physical condition of the person and to communicate said at least one measured physical condition to said processor; and
      a plurality of vibratory motors mounted to said flexible printed circuit board and arranged in a planar circular ring pattern on said flexible printed circuit board extending around a perimeter of said flexible printed circuit board;
      wherein said processor comprises executable instructions thereon configured to, in response to said at least one measured physical condition, selectively (i) sequentially actuate said plurality of vibrating motors in series along said circular ring pattern, and (ii) simultaneously activate multiple of said plurality of vibratory motors; and
   wherein each of sequential actuation and simultaneous actuation of said plurality of vibrating motors is automatically initiated in response to determining that said at least one measured physical condition is a negative physical condition causing discomfort to the person.

11. The system of claim 10, further comprising a remote computing device in data communication with said processor, said remote computing device having remote device executable computer instructions thereon configured to execute a control application stored thereon configured to:
   receive data from said wearable device, and
   in response to determining at said control application that said data is indicative of the person experiencing the negative physical condition, automatically instructing said processor from said control application to initiate operation of said plurality of vibratory motors.

12. The system of claim 11, wherein each one of said plurality of vibratory motors is configured for independent activation, and wherein said executable computer instructions of said control application are further configured to initiate operation of said plurality of vibratory motors in an order adapted to ameliorate said negative physical condition.

13. The system of claim 12, wherein said wearable device is configured to impart vibrations generated from said plurality of vibratory motors to the person through said flexible housing.

14. The system of claim 10, wherein said at least one sensor comprises at least a pulse oximeter sensor.

15. The system of claim 14, said at least one sensor further comprising a thermometer.

16. The system of claim 10, said wearable device further comprising:
   a microphone attached to said flexible printed circuit board; and
   a speaker attached to said flexible printed circuit board.

17. The system of claim 16, wherein said executable computer instructions of said control application are further configured to cause said speaker to play one of a plurality of sounds in response to determining that said person is experiencing a negative physical condition.

18. The system of claim 10, wherein an opening extends through a first side of said flexible housing, wherein said opening is aligned with said at least one sensor.

19. The system of claim 18, further comprising a multi-sided adhesive on said first side of said flexible housing adapted for removable application of said wearable device to the person's skin.

* * * * *